United States Patent
Battistini et al.

[11] Patent Number: 6,147,073
[45] Date of Patent: Nov. 14, 2000

[54] SUBSTITUTED TETRALYMETHYLEN-OXINDOLES ANALOGUES AS TYROSINE KINASE INHIBITORS

[75] Inventors: Carlo Battistini, Novate Milanese; Antonella Ermoli, Buccinasco; Sergio Vioglio, Cusano Milanino; Franco Buzzetti, Monza; Dario Ballinari, San Donato Milanese, all of Italy

[73] Assignee: Pharmacia & Upjohn S.p.A., Milan, Italy

[21] Appl. No.: 08/981,473

[22] PCT Filed: May 15, 1997

[86] PCT No.: PCT/EP97/02672

§ 371 Date: Jan. 12, 1998

§ 102(e) Date: Jan. 12, 1998

[87] PCT Pub. No.: WO97/45409

PCT Pub. Date: Dec. 4, 1997

[30] Foreign Application Priority Data

May 24, 1996 [GB] United Kingdom .................. 9610964

[51] Int. Cl.[7] ................. A61K 31/54; C07D 413/06; C07D 401/06; C07D 209/34
[52] U.S. Cl. ................. 514/235.2; 514/323; 514/418; 544/144; 546/201; 548/486
[58] Field of Search ............... 548/486; 544/144; 546/201; 514/235.2, 323, 418

[56] References Cited

U.S. PATENT DOCUMENTS 5,409,949  4/1995  Buzzetti et al. .................. 514/414

Primary Examiner—Joseph McKane
Assistant Examiner—Ebenezer Sackey
Attorney, Agent, or Firm—Oblon, Spivak, McClelland, Maier & Neustadt, P.C.

[57] ABSTRACT

A tetralylmethylene-2-oxindole derivative having the following formula (I)

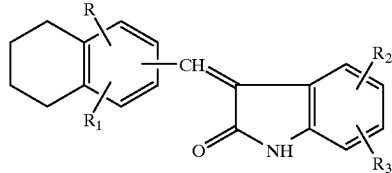

wherein
one or two of R, $R_1$, $R_2$ and $R_3$ the said two being the same or different, are selected from:
a) $-X-(CH_2)_m-NH_2$, $-X-(CH_2)_m-NR_4R_5$ or $-X-(CH_2)_m-NHR_6$, in which X is $-O-$, $-S-$ or $-NH-$, m is an integer of 2 to 4, one of $R_4$ and $R_5$ is hydrogen or $C_1-C_6$ alkyl and the other is $C_1-C_6$ alkyl or $R_4$ and $R_5$ taken together with the N atom to which they are linked form a 5 to 7 membered saturated heteromonocycle, and $R_6$ is $C_2-C_6$ alkanoyl or a C-terminally linked peptidyl residue containing from 1 to 3 aminoacids wherein the terminal amino group is either free or protected or in an alkylated form to provide a $-NR_4R_5$ group in which $R_4$ and $R_5$ are as defined above.

16 Claims, No Drawings

SUBSTITUTED TETRALYMETHYLEN-OXINDOLES ANALOGUES AS TYROSINE KINASE INHIBITORS

This is a 371 of PCT/EP97/02672 filed May 15, 1997.

The present invention relates to new derivatives of substituted tetralylmethylen-oxindoles, to a process for their preparation, to pharmaceutical compositions containing them and to their use as therapeutic agents, in particular as tyrosine kinase inhibitors.

International applications WO91/13055 and WO95/01349 disclose tetralylmethylen-oxindole derivatives endowed with high in vitro tyrosine kinase inhibiting activity. However, such tetralylmethylene-oxindole derivatives, similarly to other known tyrosine kinase inhibitors, are characterized by high lipophylicity, low aqueous solubility and consequently low bioavailability.

However, the task to combine in the same molecule a high tyrosine kinase inhibiting activity and adequate hydrosolubility cannot be achieved by merely introducing hydrophilic groups into the structure of in vitro active tyrosine kinase inhibitors, as this strategy results in most cases in a significant loss of inhibitory activity. Indeed, as known in the art, the therapeutic efficacy of all drugs is strongly influenced by different parameters that can affect their bioavailability. Object of the present invention is therefore to provide novel tetralylmethylen-oxindole compounds endowed with improved bioavailability.

Accordingly, the present invention provides novel substituted tetralylmethylene-2-oxindole derivatives having the following formula (I)

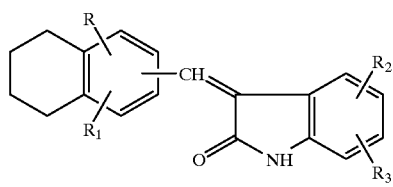

(I)

wherein one or two of R, $R_1$, $R_2$ and $R_3$ are a substituent selected independently from:

a) $-X-(CH_2)_m-NH_2$, $-X-(CH_2)_m-NR_4R_5$ or $-X-(CH_2)_m-NHR_6$ group, in which X is $-O-$, $-S-$ or $-NH-$, m is an integer of 2 to 4, one of $R_4$ and $R_5$ is hydrogen or $C_1-C_6$ alkyl and the other is $C_1-C_6$ alkyl or $R_4$ and $R_5$ taken together with the N atom to which they are linked form a 5 to 7 membered saturated heteromonocycle, and $R_6$ is $C_2-C_6$ alkanoyl or a C-terminally linked peptidyl residue containing from 1 to 3 aminoacids wherein the terminal amino group is either free or protected or in an alkylated form to provide a $-NR_4R_5$ group in which $R_4$ and $R_5$ are as defined above;

b) $-NH-C(=NH)-NR_4R_5$, $-NH-C(=NH)-NHR_6$, $-N=CH-NH_2$, $-N=CH-NR_4R_5$ or $-N=CH-NHR_6$ group in which $R_4$, $R_5$ and $R_6$ are as defined above;

c) $-X-(CH_2)_n-COR_7$ group wherein X is as defined above, n is an integer of 1 to 4, $R_7$ is hydroxy, amino, $C_1-C_6$ alkoxy or $-NR_4R_5$ in which $R_4$ and $R_5$ are as defined above or $R_7$ is a N-terminally linked peptidyl residue containing from 1 to 3 aminoacids;

d) $-COR_a$ or $-COR_8$ group in which $R_a$ is a N-terminally linked peptidyl residue containing from 1 to 3 aminoacids and $R_8$ is a $-(CH_2)_p-NH_2$, $-(CH_2)_p-NR_4R_5$ or $-(CH_2)_p-NHR_6$ group in which p is 1 or 2 and $R_4$, $R_5$ and $R_6$ are as defined above;

e) $-Y-CO-Y'-R_9$ group wherein each of Y and Y' which may be same or different is $-NH-$ or $-O-$ and $R_9$ is phenyl or $C_1-C_6$ alkyl unsubstituted or substituted by phenyl; and f) $-NHR_6$ or $-NHR_{10}$ group in which $R_6$ is as defined above and $R_{10}$ is an amino protective group; and the others of R, $R_1$, $R_2$ and $R_3$ are independently chosen from hydrogen, halogen, amino, hydroxy, $C_1-C6$ alkyl, $C_1-C_6$ alkoxy, carboxy, $C_1-C_6$ alkoxycarbonyl, $C_2-C_6$ alkanoyloxy, cyano and $-NR_4R_5$ in which $R_4$ and $R_5$ are as defined above, and the pharmaceutically acceptable salts of salt forming compounds of formula (I).

The invention includes within its scope all the possible isomers, stereoisomers and in particular Z- and E-isomers and their mixtures, and the metabolites and the metabolic precursors or bio-precursors (otherwise known as prodrugs) of the compounds of formula (I).

A$-(CH_2)-$group may be a branched or straight $C_1-C_4$ alkylene chain, typically $-CH_2-$, $-CH(CH_3)-$, $-CH_2CH_2-$ and $(CH_3)_2CH-CH<$ in particular $-CH_2-$ and $-CH(CH_3)-$.

The alkyl groups, and the alkyl moiety in the alkanoyl groups, may be branched or straight alkyl chains. A $C_1-C_6$ alkyl group is preferably a $C_1-C_4$ alkyl group, e.g. methyl, ethyl, propyl, isopropyl, butyl, sec-butyl or tert-butyl, in particular methyl or ethyl.

A $C_1-C_6$ alkoxy group is e.g. methoxy, ethoxy, propoxy, isopropoxy, butoxy or tert-butoxy, preferably methoxy, ethoxy or propoxy.

When $R_4$ and $R_5$ taken together with the nitrogen atom to which they are linked form a 5 to 7 membered saturated heteromonocycle, said ring can optionally contain a further heteroatom chosen from nitrogen, oxygen and sulphur. Typically said ring is a pyrrolidine, piperidine or morpholine ring. Examples of aminoacids, which form the peptidyl residue according to the meaning of $R_a$, $R_6$ and $R_7$ as given above, are alanine, glycine, histidine, threonine, glutamic acid, aspartic acid and tyrosine; preferably glycine, alanine, threonine and glutamic acid. Accordingly, the $R_6$ peptidyl residue may be selected, for instance, from the groups including $-CO-CH(CH_3)-NH_2$, $-CO-CH(CH_3)-NHCO-CH(CH_3)-NH_2$, $-CO-CH(NH_2)-CHOH-CH_3$, $-CO-CH(NH_2)-CH_2-CH_2-COOH$, $-CO-CH_2-NH_2$, $-CO-CH_2-NH-CO-CH_2-NH_2$, $-CO-CH(CHOH-CH_3)-NH-CO-CH(NH_2)-CHOH-CH_3$, and $-CO-CH(CH_2-CH_2-COOH)-NH-CO-CH(NH_2)-CH_2-CH_2-COOH$, in which the terminal amino group may be either free or in a protected or alkylated form as stated above.

Similarly the $R_a$ or $R_7$ peptidyl residues are for instance a group selected independently from $-NH-CH(CH_3)-COOH$, $-NH-CH_2-COOH$, $-NH-CH(COOH)-CHOH-CH_3$, $-NH-CH(CH_3)-CONH-CH(CH_3)-COOH$, $-NH-CH(COOH)-CH_2-CH_2-COOH$, $-NH-CH(COOH)-CH_2-COOH$ and $-NH-CH(COOH)-CH_2-Ph$.

When $R_6$ is a C-terminally linked peptidyl residue group as defined above in which the terminal amino group is in a protected form, said amino group may be protected in a conventional way as known from the chemistry of peptides. Typically by an amino protecting group chosen from benzyloxycarbonyl, p-methoxybenzyloxycarbonyl, tert-butoxycarbonyl (BOC), biphenylisopropoxycarbonyl (BBOC), 9-fluorenylmethoxycarbonyl (Fmoc), triphenylmethyl (Trityl), O-nitrobenzenesulfenyl (Nps), trimethylsilylethoxycarbonyl, di-p-nitrophenylethoxycarbonyl and trichloroethoxycarbonyl (Troc). Preferably said amino protecting group being chosen from tert-butoxycarbonyl (BOC) and 9-fluorenylmethoxycarbonyl (Fmoc).

A—(CH$_2$)— group may be, for instance, a —CH$_2$—, —CH$_2$—CH$_2$— or —CH(CH$_3$)—, preferably —CH$_2$— or —CH(CH$_3$)—.

When R$_9$ is C$_1$–C$_6$ alkyl substituted by phenyl, it is preferably a phenyl-C$_1$–C$_4$ alkyl group, in particular benzyl or phenethyl. A halogen atom is for instance fluorine, chlorine, bromine or iodine, preferably a fluorine, chlorine or bromine atom.

A C$_2$–C$_6$ alkanoyl group or an alkanoyl moiety in alkanoyloxy groups is preferably a C$_2$–C$_4$ alkanoyl group, in particular acetyl, propionyl or butyryl.

The term tetralin is meant to refer to 5,6,7,8-tetrahydronaphthalene.

Pharmaceutically acceptable salts of the compounds of the invention include acid addition salts with inorganic acids, e.g. nitric, hydrochloric, hydrobromic, sulphuric, perchloric and phosphoric acid or organic acids, e.g. acetic, trifluoracetic, propionic, glycolic, lactic, oxalic, malonic, malic, maleic, tartaric, citric, benzoic, cinnamic, mandelic and salicylic acid, and salts with inorganic bases, e.g. alkali metal, especially sodium or potassium bases or alkaline earth metal, especially calcium or magnesium bases, or with organic bases, e.g. alkylamines, preferably triethylamine.

As stated above, the present invention also includes within its scope pharmaceutically acceptable bio-precursors (otherwise known as prodrugs of the compounds) of formula (I), i.e. compounds which have different formula to formula (I) above but which, nevertheless, upon administration to a human being are converted directly or indirectly in vivo into a compound of formula (I).

Preferred compounds of the invention are the compounds of formula (I), wherein one of R, R$_1$, R$_2$ and R$_3$ is independently a substituent selected from a') —X—(CH$_2$)$_m$—NH$_2$, —X—(CH$_2$)$_m$—NR$_4$R$_5$ or —X—(CH$_2$)$_m$—NHR$_6$ in which X is oxygen or —NH—, m is 2, one of R$_4$ and R$_5$ is C$_1$–C$_4$ alkyl and the other is hydrogen or C$_1$–C$_4$ alkyl or R$_4$ and R$_5$ taken together with the nitrogen atom to which they are linked form a piperidine or morpholine ring, and R$_6$ is a C-terminally linked peptidyl residue containing 1 or 2 aminoacids;

b') —NH—C(=NH)—NR$_4$R$_5$, —N=CH—NR$_4$R$_5$ in which one of R$_4$ and R$_5$ is C$_1$–C$_4$ alkyl and the other is hydrogen or C$_1$–C$_4$ alkyl;

c') —X—(CH$_2$)$_n$—COR$_7$ in which X is —O— or —NH—, n is 1 or 2, R$_7$ is amino or a N-terminally linked peptidyl residue containing 1 or 2 aminoacids;

d') —COR$_a$ or —COR$_8$ group in which R$_a$ is as defined above and R$_8$ is —(CH$_2$)$_p$—NH$_2$ or —(CH$_2$)$_p$—$_{NR4}$R$_5$ in which p is 1 or 2 and one of R$_4$ and R$_5$ is C$_1$–C$_4$ alkyl and the other is hydrogen or C$_1$–C$_4$ alkyl or R$_4$ and R$_5$ taken together with the nitrogen atom to which they are linked form a piperidine or morpholine ring; and e') —NHR$_6$ or —NHR$_{10}$ in which R$_6$ is C$_2$–C$_4$ alkanoyl or a C-terminally linked peptidyl residue containing 1 or 2 aminoacids and R$_{10}$ is an amino protecting group; and the others of R, R$_1$, R$_2$ and R$_3$ are independently chosen from hydrogen, halogen, amino, hydroxy, C$_1$–C$_4$ alkyl, C$_1$–C$_4$ alkoxy, C$_1$–C$_4$ alkoxy-carbonyl, C$_2$–C$_4$ alkanoyloxy, cyano and C$_1$–C$_4$ alkylamino or di-C$_1$–C$_4$ alkylamino; and the pharmaceutically acceptable salts of salt forming compounds of formula (I).

Examples of preferred specific compounds of formula (I) are the following compounds:

5-(tert-butoxycarbonylamino)-3-(1,4-dihydroxy-2-tetralylmethylen)-2-oxindole;

5-glycylamino-3-(1,4-dihydroxy-2-tetralylmethylen)-2-oxindole;

5-(glycylglycylamino)-3-(1,4-dihydroxy-2-tetralylmethylen)-2-oxindole;

5-(alanylamino)-3-(1,4-dihydroxy-2-tetralylmethylen)-2-oxindole;

5-(alanylalanylamino)-3-(1,4-dihydroxy-2-tetralylmethylen)-2-oxindole;

5-(N-tert-butoxycarbonylalanylamino)-3-(1,4-dihydroxy-2-tetralylmethylen)-2-oxindole;

5-(threonylamino)-3-(1,4-dihydroxy-2-tetralylmethylen)-2-oxindole;

5-(glutamylamino)-3-(1,4-dihydroxy-2-tetralylmethylen)-2-oxindole;

5-(2-dimethylaminoethylamino)-3-(1,4-dihydroxy-2-tetralylmethylen)-2-oxindole;

5-(2-morpholinoethylamino)-3-(1,4-dihydroxy-2-tetralylmethylen)-2-oxindole;

5-(2-glycylaminoethylamino)-3-(1,4-dihydroxy-2-tetralylmethylen)-2-oxindole;

5-(2-alanylamino-ethylamino)-3-(1,4-dihydroxy-2-tetralylmethylen)-2-oxindole;

5-(3,3-dimethylguanidino)-3-(1,4-dihydroxy-2-tetralylmethylen)-2-oxindole;

5-(dimethylaminomethylenamino)-3-(1,4-dihydroxy-2-tetralylmethylen)-2-oxindole;

N-[3-(1,4-dihydroxy-2-tetralylmethylen)-2-oxindol-5-yl] glycyl-alanine;

N-[3-(1,4-dihydroxy-2-tetralylmethylen)-2-oxindol-5-yl] glycyl-glycine;

N-[3-(1,4-dihydroxy-2-tetralylmethylen)-2-oxindol-5-ylcarbonyl]glycine;

N-[3-(1,4-dihydroxy-2-tetralylmethylen)-2-oxindol-5-ylcarbonyl]alanine;

5-(2-aminoacetyl)-3-(1,4-dihydroxy-2-tetralylmethylen)-2-oxindole;

5-(2-morpholinoacetyl)-3-(1,4-dihydroxy-2-tetralylmethylen)-2-oxindole;

3-[4-(2-glycylaminoethoxy)-1-tetralylmethylen])-2-oxindole;

3-[4-(2-alanylaminoethoxy)-1-tetralylmethylen]-2-oxindole;

3-[4-(2-morpholinoethoxy)-1-tetralylmethylen]-2-oxindole;

N-[1-(2-oxindol-3-ylmethylen)-4-tetralyloxyacetyl]glycine;

3-(4-glycylamino-1-tetralylmethylen)-2-oxindole; and 3-(4-alanylamino-1-tetralylmethylen)-2-oxindole;

which, when appropriate, may be either a Z- or E-diastereoisomer or Z,E- mixtures thereof; and the pharmaceutically acceptable salts of salt forming members of the group.

The compounds of formula (I), and the salts thereof, can be obtained by a process comprising:

a) reacting an aldehyde of formula (II)

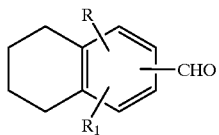
(II)

wherein R and R$_1$ are as defined above, with a compound of formula (III)

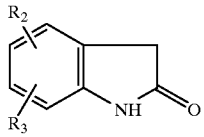
(III)

wherein R$_2$ and R$_3$ are as defined above; or b) reacting a compound of formula (IV)

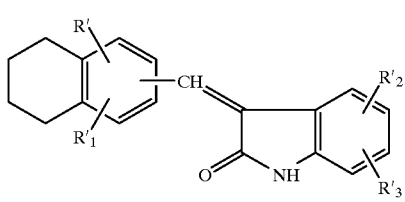
(IV)

wherein one or two of R', R'$_1$, R'$_2$ and R'$_3$ are OH, —NH$_2$ or —SH and the others are as R, R$_1$, R$_2$ and R$_3$ as defined above, with an alkylating agent of formula (V) selected from Z—(CH$_2$)$_m$—NH$_2$;

Z—(CH$_2$)$_m$—NR$_4$R$_5$;

Z—(CH$_2$)$_m$—NHR$_6$; and

Z—(CH$_2$)$_n$—COR$_7$.

in which Z is a halogen atom and m, n, R$_4$, R$_5$, R$_6$ and R$_7$ are as defined above, thus obtaining a compound of formula (I) wherein one or two of R, R$_1$, R$_2$ and R$_3$ are as defined above under a) or c); or c) reacting a compound of formula (VI)

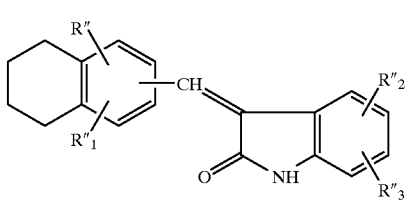
(VI)

wherein one or two of R", R"$_1$, R"$_2$ and R"$_3$ are —OH or —NH$_2$ and the others are as R, R$_1$, R$_2$ and R$_3$ as defined above, with an acylating agent of formula (VII) selected from

HOOC—Y'—R$_9$

HOOC—R$_a$;

HOOC—R$_8$;

or a reactive carbonyl derivative thereof, wherein R$_a$, R$_8$, Y' and R$_9$ are as defined above, thus obtaining a compound of formula (I) wherein one or two of R, R$_1$, R$_2$ and R$_3$ are as defined above under d) or e); and, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound of formula (I), and/or, if desired, separating a mixture of isomers of a compound of formula (I) into the single isomers.

The reaction of a compound of formula (II) with a compound of formula (III) is an analogy process which can be carried out according to known methods as herebelow described; preferably in the presence of a basic catalyst, e.g. pyridine, piperidine, dimethylamine, or a suitable alkali metal hydroxide or alkoxide. For example the reaction of a compound of formula (II) with a compound of formula (III) may be carried out under the conditions of the Knoevenagel reaction as described e.g. by G. Jones in Organic Reactions 15, 204 (1967). Suitable catalysts are organic bases such as pyridine, piperidine or diethylamine. The condensation may be performed in an inert organic solvent, e.g. pyridine, ethanol, methanol, benzene, or dioxane at temperatures ranging from about 0 to about 100° C. Preferably the reaction is carried out in warm ethanol solution in the presence of a piperidine catalyst.

In a compound of formula (V) the halogen atom Z is for instance iodine, bromine or chlorine, preferably bromine. Alkylation of a compound of formula (IV) can be carried out according to known methods, for instance by salification with sodium hydride and then reaction with the bromide of formula (V) in a high boiling aromatic solvent such as xylene. A reactive derivative of a carboxylic acid of formula (VII) is for instance an acyl halide or an anhydride (typically a mixed anhydride) or an in situ generated activated form of the carboxylic acid with a coupling reagent such as benzotriazol-1-yloxy-tripyrrolidinophosphonium hexafluorophosphate (PyBOP). The acylation reaction of a compound of formula (VI) with a compound of formula (VII) is preferably carried out in the presence of a basic agent such as pyridine, at a temperature ranging from about 0 to about 50° C.

A compound of formula (I) can be converted into another compound of formula (I) according to known methods. For instance, a compound of formula (I) in which one or two of R, R$_1$, R$_2$ and R$_3$ are carboxy and the others are as defined above, can be converted into a corresponding compound of formula (I) wherein one or two of R, R$_1$, R$_2$ and R$_3$ are a COR$_a$ group in which R$_a$ is as defined above, by acylation reaction with a suitable aminoacid or peptide in an organic solvent, e.g. dichloromethane, in the presence of a basic agent such as pyridine or N-methylmorpholine.

A compound of formula (I) wherein one or two of R, R$_1$, R$_2$ and R$_3$ are amino and the others are as defined above, can be converted into another compound of formula (I) in which one or two of R, R$_1$, R$_2$ and R$_3$ are —NH—C(=NH)—NH$_2$, for instance by reaction with di-tert-butoxycarbonylthiourea according to known methods. The guanidino substituted compound thus obtained can be in its turn converted into another compound of formula (I) in which one or two of R, R$_1$, R$_2$ and R$_3$ are a group —NH—C(=NH)—NR$_4$R$_5$ or —NH—C(=NH)—NHR$_6$ in which one or two of R$_4$ and R$_5$ are C$_1$–C$_6$ alkyl and R$_6$ is as defined above, according to well known alkylation or acylation methods, respectively. Similarly a compound of formula (I) wherein one or two of R, R$_1$, R$_2$ and R$_3$ are amino and the others are as defined above, can be converted according to known methods into another compound of formula (I) wherein one or two of R, R$_1$, R$_2$ and R$_3$ are a —N=CHNR$_4$R$_5$ group. For instance an amino substituted compound can be reacted with a suitable di- (C$_1$–C$_6$ alkyl)N—CHO aldehyde in a suitable polar solvent, e.g. a lower alkanol, typically methanol or ethanol, in the presence of a basic agent, such as piperidine, to obtain a —N=CHNR$_4$R$_5$ compound in which R$_4$ and R$_5$ are C$_1$–C$_6$ alkyl.

The optional salification of a compound of formula (I) as well as the conversion of a salt into the free compound and the separation of a mixture of isomers into the single isomers may be carried out by conventional methods. For example, the separation of a mixture of geometric isomers, e.g. cis- and trans-isomers, may be carried out by fractional crystallization from a suitable solvent or by chromatography, either column chromatography or high pressure liquid chromatography. The intermediates of formulae (II) and (III) can be obtained by known methods from known compounds, e.g. as described in WO91/13055 and WO95/01349. The people skilled in the art will appreciate that the intermediates of formula (II) and (III) can be submitted to the same substituent chemical modifications as described in connection with the compounds of formula (I). However, these substituent modifications can be properly performed at convenience at different levels within the process depending on the nature of the substituents and on the compatibility of the transforming reaction with the involved chemical groups. The intermediate compounds of formulae (IV), (V), (VI) and (VII) are known compounds or can be obtained from known compounds. For instance, most of the compounds of formulae (IV) and (VI) are known from WO91/13055 and WO95/01349 or can be obtained similarly.

Compounds of formula (III) if not available, can also be obtained from the corresponding indole derivative by an analogy process through known methods. A preferred one is an oxidation-reduction process as described by Marfat et al. in Tetrahedron Letters 28, 4027 (1987) comprising the use of pyridinium bromide perbromide using a tertiary alcohol as solvent, preferably tert-butanol, followed by a reductive step with zinc in acetic acid or hydrogenation in the presence of palladium on charcoal.

When in the new compounds of the present invention and in the intermediate products used for their preparation there are groups present which need to be protected before the above described reactions are performed, they may be protected before the reaction takes place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence, the compounds according to the present invention can be useful in the treatment of pathological proliferation disorders in mammals, including humans. Typical examples of such disorders are tumors, including leukemia, and psoriasis. The compounds of the invention can also be useful in inhibiting the development of the atheromatous plaque and in the control of angiogenesis and as anti-metastatic agents.

Recent studies on the molecular basis of the neoplastic transformation have identified a family of genes, designed oncogenes, whose aberrant expression causes tumorigenesis. For example, the RNA tumor viruses possess such an oncogene sequence whose expression determines neoplastic conversion of infected cells. Several of their oncogene-encoded proteins, such as pp60$^{v\text{-}src}$, p70$^{gag\text{-}yes}$, p130$^{gag\text{-}fps}$ and p70$^{gag\text{-}fgr}$ display protein tyrosine kinase activity, that is they catalyze the transfer of the 1-phosphate from adenosine triphosphate (ATP) to tyrosine residues in protein substrate. In normal cells, several growth factor receptors, for example the receptors for PDGF, EGF, α-TGF and insulin, display tyrosine kinase activity. Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiation and it can be effective in the prevention and chemotherapy of cancer and in other pathological proliferative conditions.

Hence the compounds according to the present invention can be useful in the treatment of pathological proliferation disorders in mammals, including humans.

A human or animal, e.g. a mammal, can thus be treated by a method comprising the administration thereto of therapeutically effective amount of one of the compounds of the invention. In this way the condition of the human or animal may be improved. Amelioration of the disease state or disorder from which the human or animal is suffering can,be achieved. Typical examples of such disorders are benign and malignant tumours, including leukaemia such as myeloblastic leukaemia, lymphoma, sarcoma, neuroblastoma, Wilm's tumour, malignant neoplasm of the bladder, breast, lung or thyroid, neoplasias of epithelial origin, such as mammacarcinoma. Moreover, they can be useful in the treatment of epidermal hyperproliferation, such as psoriasis. The compounds of the invention can also be useful in inhibiting the development of the atheromatous plaque and restenosis, in the control of angiogenesis, as anti-metastatic agents and in treating diabetic complications. They have also utility in the control of immune system diseases, e.g. as immunosuppressants, since protein tyrosine kinases, particularly Zap70, p56lck and p59 fyn, are strongly involved in the control of the proliferation of the immune system. Moreover, the ocmpounds of the invention have utility in the treatment of Alzheimer's disease due to the pivotal role played by tyrosine phosphorylation (e.g., Tau proteins) in the development of this disease.

The tyrosine specific protein kinase activity of the compounds of the invention is shown, e.g., by the fact that they are active in the in vitro and in vivo test described herebelow.

In Vitro Assay p45 v-abl Kinase Purification

The enzyme used in our tests is the p45 v-abl tyrosine kinase which represents the catalytic domain of the Abelson tyrosine kinase (isolated from the Abelson murine leukemia virus). The p45 v-abl kinase is produced and isolated as described by Wang et al. in *J.Biol.Chem.* 260, 64 (1985) and by Ferguson et al. in *J.Biol.Chem.* 260, 3652 (1985) and in *Biochem.J.* 257, 321 (1989).

p45 v-abl Kinase Assay (Val⁵)-angiotensin II phosphorylation is performed by incubation with 40 ng of purified abl-kinase and $(\gamma$-$^{32}$P) ATP, in 50 µl of buffer containing Tris-HCl 25 mM, pH 8.0, MgCl$_2$ 10 mM and dithiothreitol 0.1 mM (kinase buffer). The reaction mixture is incubated for the indicated time at 30° C. and the reaction stopped by adding 50 µl of 5% trichloracetic acid. After a brief incubation on ice the tubes are centrifuged. The supernatants are spotted on phosphocellulase paper squares (Whatman P-81) and washed extensively in acetic acid. The radioactivity bound to dried phosphocellulose squares is measured in a liquid scintillation counter. IC$_{50}$ values are calculated from triplicated determination of each experimental point. Each inhibitor is tested at concentrations ranging from 0 to 400 µg in the presence of fixed concentrations of peptide (2 mM) and ATP (50 µM).

In Vivo Assay

K562 Cell Growth Inhibition Assay

K562 cells, a human myelogenous leukemia cell line, were seeded into a 24 wells tissue culture plate (Falcon 3047) (10000/well) in the presence of increasing concentrations of the compounds.

After 72 h, cells were harvested and were counted using a cell counter (Coulter Counter-ZM). The percent of inhibition was evaluated in respect to the untreated control cells.

The inhibitory activity data for a representative group of compounds according to the present invention, obtained both in the in vitro p45 v-abl kinase assay and in the in vivo human chronic myeloid leukemia K562 cell growth inhibition assay described above, are set out in the following Table 1.

TABLE 1

| Compound | IC$_{50}$ (µM) | |
|---|---|---|
| | v-abl | K562 |
| 5-(glutamylamino)-3-(1,4-dihydroxy-2-tetralylmethylen)-2-oxindole | 10 | 5.97 |
| 5-(alanylamino)-3-(1,4-dihydroxy-2-tetralylmethylen)-2-oxindole | 10 | 8.31 |
| 5-(N-tert-butyoxycarbonylalanylamino)-3-(1,4-dihydroxy-2-tetralylmethylene)-2-oxindole | 1.56 | 5.86 |
| 5-(alanylalanylamino)-3-(1,4-dihydroxy-2-tetralylmethylene)-2-oxindole trifluoroacetate | 3.12 | 5.30 |

As can be appreciated from the activity data shown in Table 1, the compounds according to the invention are endowed with valuable biological properties.

Moreover, in every case the water solubility of the compounds of the invention is greater than 10 mg/ml, thus allowing to prepare aqueous solutions with concentration higher than 10 mmol, in striking difference with the compounds of the above cited prior art, which on the contrary are characterized by relatively low water solubility.

In view of their high activity, the compounds of the invention can be used in medicine in treating a patient in need of tyrosine kianse inhibition.

The compounds of the invention can be administers in a variety of dosage forms, e.g. orally, in the forms of tablets, capsules, sugar- and film-coated tablets, liquid solutions or suspensions; rectally, in the form of suppositories; parenterally, e.g. intramuscularly, or by intravenous injection or infusion; or topically. The dosage depends on the age, weight, condition of the patient and administration route. For example, the dosage adopted for oral administration to adult humans for the compound 5-(alanylamino)-3-(1,4-dihydroxy-2-tetralylmethylen)-2-oxindole may range from about 5 to about 150–200 mg per dose, from 1 to 5 times daily. Of course, these dosage regimes may be adjusted to provide the optimal therapeutic response. The invention includes pharmaceutical compositions comprising a compound of formula (I) or a pharmaceutically acceptable salt thereof and a pharmaceutically acceptable excipient (which can be a carrier or diluent).

The pharmaceutical compositions containing the compounds of the invention are usually prepared following conventional methods and are administered in a pharmaceutically suitable form. For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, by means of mixing, granulating, tabletting, sugar-coating or film-coating processes. The liquid dispersion for oral administration may be, e.g., syrups, emulsions and suspensions.

The syrup may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or, preferably, they may be in the form of sterile aqueous, isotonic saline solutions.

The suppositories may contain, together with the active compound, a pharmaceutically acceptable carrier, e.g. cocoabutter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

A further object of the present invention is a combined method of treatment of cancer or of amelioration of the conditions of mammals, including humans, suffering from cancer, said method comprising administering 1) a compound of the invention, that is a compound of formula (I), or a pharmaceutically acceptable salt thereof, and 2) an additional antitumor agent, in amounts and close enough together in time sufficient to produce a therapeutically useful effect.

The present invention also provides products containing a compound of the invention, that is a compound of formula (I) or a pharmaceutically acceptable salt thereof, and an additional antitumor agent as a combined preparation for simultaneous, separate or sequential use in anticancer therapy.

The term "antitumour agent" is meant to comprise both a single antitumour drug and "cocktails", i.e. a mixture of such drugs, according to the clinical practice. Examples of antitumour agents that can be formulated with a compound of the invention or, alternatively, can be administered in a combined method of treatment, include doxorubicin, daunomycin, epirubicin, idarubicin, etoposide, fluorouracil, melphalan, cyclophosphamide, bleomycin, vinblastin and mitomycin or a mixture of two or more thereof. The compounds of the invention can therefore be used in a treatment to ameliorate a cancer. They may be administered to a patient suffering from a cancer treatable with an antitumour agent, for example an anthracycline glycoside such as doxorubicin, daunomycin, epirubicin or idarubicin as mentioned above, together with the antitumour agent.

A compound of the invention and an antitumour agent such as an anthracycline glycoside can be administered to improve the condition of a patient having leukemia such as myeloblastic leukemia, lymphoma, sarcoma, neuroblastoma, Wilm's tumour or malignant neoplasm of the bladder, breast, lung or thyroid. Accordingly, the present invention provides a method of treating a patient in need of a tyrosine kinase inhibitor, the method comprising administering to said patient a therapeutically effective amount of a compound of formula (I) as defined above, or a pharmaceutically acceptable salt thereof.

The following examples illustrate but do not limit the invention.

EXAMPLE 1

5-(tert-butoxycarbonylamino)-3-(1,4-dihydroxy-2-tetralylmethylen)-2-oxindole

A solution of 1,4-dihydroxytetralin-2-aldehyde (120 mg, 0.62 mM), 5-tert-butoxycarbonylamino-2-oxindole (150 mg, 0.60 mM) in anhydrous alcohol (20 ml) containing piperidine catalyst (0.02 ml, 0.2 mM) was refluxed for 2 h. The ethanol was evaporated under vacuum and the residue purified by flash chromatography using cyclohexane/ethylacetate 2:1 as eluant. Thus pure title compound was obtained in 59% yield (150 mg).

$C_{24}H_{26}N_2O_5$ calcd: C68.23 H6.20 N6.63 found: C68.05 H6.22 N6.55

FD-MS: 423 (59, [MH]+), 422 (100, [M]+), 322 (12, [M-BOC+H]+)

NMR δ ppm (200 MHz, DMSO): 1.47 (s, $9H_{E+Z}$), 1.67 (M, $4HE_{E+Z}$) 2.55 (M, $4H_{E+Z}$), 6.82 (t, J=7.8 HZ, $1H_E$), 6.93 (m, $1H_{E+Z}$), 7.3–7.6 (m, $2H_{E+Z}$), 7.69 (s, $1H_E$), 7.70 (s, $1H_Z$), 7.92 (s, $1H_Z$), 8.32 (s, $1H_E$), 8.62 (two bs, $1H_{E+Z}$), 8.68 (s, $1H_Z$), 8.79 (s, $1H_Z$), 8.92 (s, $1H_E$), 10.15 (s, 1H), 10.32 (s, 1H).

By proceeding analogously the following compounds can be prepared:

5-(2-dimethylaminoethylamino)-3-(1,4-dihydroxy-2-tetralylmethylen)-2-oxindole;

5-(2-morpholinoethylamino)-3-(1,4-dihydroxy-2-tetralylmethylen)-2-oxindole;

5-(3,3-dimethylguanidino)-3-(1,4-dihydroxy-2-tetralylmethylen)-2-oxindole;

5-(dimethylaminomethylenamino)-3-(1,4-dihydroxy-2-tetralylmethylen)-2-oxindole;

N-[3-(1,4-dihydroxy-2-tetralylmethylen)-2-oxindol-5-yl) glycyl-alanine;

N-[3-(1,4-dihydroxy-2-tetralylmethylen)-2-oxindol-5-yl] glycyl-glycine;

N-[3-(1,4-dihydroxy-2-tetralylmethylen)-2-oxindol-5-ylcarbonyl]glycine;

N-[3-(1,4-dihydroxy-2-tetralylmethylen)-2-oxindol-5-ylcarbonyl]alanine;

5-(2-aminoacetyl)-3-(1,4-dihydroxy-2-tetralylmethylen)-2-oxindole;

5-(2-morpholinoacetyl)-3-(1,4-dihydroxy-2-tetralylmethylen)-2-oxindole;

3-[4-(2-morpholinoethoxy)-1-tetralylmethylen]-2-oxindole; and

N-[1-(2-oxindol-3-ylmethylen)-4-tetralyloxyacetyl]glycine.

EXAMPLE 2

5-amino-3-(1,4-dihydroxy-2-tetralylmethylen)-2-oxindole trifluoroacetate

To a solution of 5-(tert-butoxycarbonylamino)-3-(1,4-dihydroxy-2-tetralylmethylen)-2-oxindole (422 mg, 1 mM) in dichloromethane (4.2 ml) was added trifluoroacetic acid (4.2 ml) and the resulting solution kept for 1 h at room temperature. The solution was evaporated to dryness, the remaining oil triturated with ethyl ether, the solid residue filtered and washed with ice-cold ether. Thus almost pure title compound was obtained in about 90% yield (321 mg).

$C_{21}H_{19}F_3N_2O_5$ calcd: C57.80 H4.39 N6.42 F13.06 found: C57.75 H4.29 N6.35 F13.01

FD-MS: 323 (55, [MH]+), 322 (100, (M]+)

NMR δ ppm (400 MHz, DMSO): 1.69 (m, 4H), 2.58 (m, 4H), 6.86 (s, 1H), 6.94 (d, J=8.2 Hz, 1H), 7.15 (dd, J=8.2/2.1 Hz, 1H), 7.60 (d, J=2.1 Hz, 1H), 7.75 (s, 1H), 8.4 (bs, 1H), 8.9 (bs, 1H), 9.7 (bs, 3H), 10.71 (s, 1H).

EXAMPLE 3

5-(glutamylamino)-3-(1,4-dihydroxy-2-tetralylmethylen)-2-oxindole trifluoroacetate To a suspension of 5-amino-3-(1,4-dihydroxy-2-tetralylmethylen)-2-oxindole (140 mg, 0.43 mM) and N-tert-butoxycarbonyl-L-glutamic acid tert-butylester (180 mg, 0.55 mM) in THF (12 ml) were added benzotriazol-1-yloxytripyrrolidinophosphonium hexafluorophosphate (290 mg, 0.55 mM) and N-methylmorpholine (0.06 ml, 0.55 mM). The mixture was stirred for 4 h at room temperature, then the mixture was evaporated to dryness, the residue was purified by gradient elution chromatography on silica gel using cyclohexane/ethylacetate 50–66%. Thus almost pure 5-(N-tert-butoxycarbonyl-L-glutamylamino)-3-(1,4-hydroxy-2-tetralylmethylen)-2-oxindole was obtained, which was deprotected with trifluoroacetic acid as described in Example 2 to give pure title compound in about 40% yield (92 mg). $C_{26}H_{26}F_3N_3O_6$ calcd: C58.53 H4.91 F10.68 N7.88 found: C58.45 H4.85 F10.70 N7.65

FAB-MS: 452 (100, [MH]+), 323 (65, [MH-COCH $(CH_2CH_2COOH)NH_2$+H]+)

NMR δ ppm (400 MHz, DMSO): 1.68 (m, 4H), 1.8–2.1 (m, 2H), 2.33 (m, 2H), 2.57 (m, 4H), 3.78 (t, J=6.6 Hz, 1H), 6.83 (d, J=8.3 Hz, 1H), 6.94 (s, 1H), 7.59 (dd, J=2,2/8.3 Hz, 1H), 7.68 (s, 1H), 7.75 (d, J=2.2 Hz, 1H), 8.3–8.9 (two bs, 2H), 10.2 (bs, 1H), 10.49 (s, 1H).

By proceeding analogously the following compounds can be prepared:

5-glycylamino-3-(1,4-dihydroxy-2-tetralylmethylen)-2-oxindole;

5-(2-glycylaminoethylamino)-3-(1,4-dihydroxy-2-tetralylmethylen)-2-oxindole;

5-(2-alanylamino-ethylamino)-3-(1,4-dihydroxy-2-tetralylmethylen)-2-oxindole;

3-[4-(2-glycylaminoethoxy)-1-tetralylmethylen])-2-oxindole;

3-[4-(2-alanylaminoethoxy)-1-tetralylmethylen]-2-oxindole;

3-(4-glycylamino-1-tetralylmethylen)-2-oxindole; and 3-(4-alanylamino-1-tetralylmethylen)-2-oxindole.

EXAMPLE 4

5-(threonylamino)-3-(1,4-dihydroxy-2-tetralylmethylen)-2-oxindole trifluoroacetate To a suspension of 5-amino-3-(1,4-dihydroxy-2-tetralylmethylen)-2-oxindole (140 mg, 0.43 mM) and N-tert-butoxycarbonyl-L-threonine (100 mg, 0.55 mM) in THF (12 ml) were added benzotriazol-1-yloxy tripyrrolidinophosphonium hexafluorophosphate (290 mg, 0.55 mM) and N-methylmorpholine (0.06 ml, 0.55 mM) . The mixture was stirred for 4 h at room temperature. Then the mixture was evaporated to dryness and the residue purified by column chromatography on silica gel using gradient elution (cyclohexane/ethylacetate 50–66%). Thus almost pure 5-(N-t-butoxycarbonyl-L-threonylamino)-3-(1,4-dihydroxy-2-tetralylmethylen)-2-oxindole was obtained, which was deprotected with trifluoroacetic acid as described in Example 2 to give pure title compound in about 50% yield (116 mg).

$C_{25}H_{26}F_3N_3O_7$ calcd: C55.87 H4.88 F10.60 N7.82 found: C55.65 H4.55 F10.61 N7.75

FD-MS: 423 (100, [M]+), 322 (6, [MH-CH(CHOHCH3)NH2)+)

NMR δ ppm (400 MHz, DMSO): 1.08 (d, J=6.5 Hz, 3H), 1.67 (m, 4H), 2.56 (m, 4H), 3.11 (m, 1H), 3.88 (m, 1H), 4.8 (bs, 1H), 6.78 (d, J=8.2 Hz, 1H), 6.95 (s, 1H), 7.63 (dd, J=2.1 Hz, J=8.2 Hz, 1H), 7.67 (s, 1H), 7.73 (d, J=2.1 Hz, 1H), 8.3–8.9 (two bs, 2H), 9.8 (bs, 1H), 10.42 (s, 1H).

EXAMPLE 5

5-(N-tert-butoxycarbonylalanylamino)-3-(1,4-dihydroxy-2-tetralylmethylen)-2-oxindole To a solution of 5-amino-3-(1,4-dihydroxy-2-tetralylmethylen)-2-oxindole (150 mg, 0.42 mM) and N-tert-butoxycarbonylalanine (95 mg, 0.5 mM) in THF (30 ml) were added benzotriazol-1-yloxytripyrrolidinophosphonium hexafluorophosphate (260 mg, 0.5 mM) and N-methylmorpholine (0.06 ml, 0.5 mM). The resulting mixture was stirred for 4 h at room temperature. Thereafter the solvent was evaporated under vacuum and the residue was purified by flash chromatography using cyclohexane/ethylacetate 1:9 as eluant.

$C_{27}H_{31}N_3O_6$ calcd: C65.70 H6.33 N8.51 found: C65.65 H6.25 N8.45

FD-MS: 493 (100, [M]+), 393 (24, [M-(CH3COCO+H]), 322 (3, [M-Ala-Boc+H]+)

NMR δ ppm (400 MHz, DMSO): 1.2 (d, J=7.0 Hz, $3H_E$), 1.25 (d, J=7.0 Hz, $3H_Z$), 1.33 (s, $9H_E$), 1.35 (s, $9H_Z$), 1.65 (m, $4H_{E+Z}$), 2.56 (m, $4H_{E+Z}$), 4.04 (m, $^1H_{E+Z}$), 6.76 (d, J=8.5 HZ, $1H_E$), 6.77 (d, J=8.5 HZ, $1H_Z$), 6.94 (s, $1H_E$), 6.97 (d, J=7.3 Hz, $1H_E$), 7.02 (d, J=7.3 Hz, $1H_Z$), 7.33 (dd, J=2.0/8.5 Hz, $1H_Z$), 7.6–7.9 (m, $3H_{E+Z}$), 8.34 (s, $1H_E$), 8.65 (s, $1H_Z$), 8.79 (s, $1H_Z$), 8.91 (s, $1H_E$), 9.70 (s, $1H_E$), 9.90 (s, $1H_Z$), 10.41 (S, $1H_E$), 10.58 (s, $1H_Z$).

EXAMPLE 6

5-(alanylamino)-3-(1,4-dihydroxy-2-tetralylmethylen)-2-oxindole trifluoroacetate 5-(N-tert-butoxycarbonylalanylamino)-3-(1,4-dihydroxy-2-tetralylmethylen)-2-oxindole (30 mg, 0.06 mM) was deprotected as described in Example 2 thus giving 24 mg of pure title compound.

FD-MS: 393 (100, [M]+), 322 (10, [M-COCH(CH3)NH2+H]+)

NMR δ ppm (400 MHz, DMSO): 1.39 (d, J=7.0 Hz, 3H), 1.67 (m, 4H), 2.56 (m, 4H), 3.88 (m, 1H), 6.83 (d, J=8.2 Hz, 1H), 6.93 (s, 1H), 7.62 (dd, J=2.1/8.2Hz, 1H), 7.68 (s, 1H), 7.72 (d, J=2.1 Hz, 1H), 8.1 (bs, 3H), 8.37 (s, 1H), 8.86 (s, 1H) 10.15 (s, 1H), 10.49 (s, 1H).

EXAMPLE 7

5-(alanylalanylamino)-3-(1,4-dihydroxy-2-tetralylmethylen)-2-oxindole trifluoroacetate To a suspension of 5-amino-2-oxindole (800 mg, 5.4 mM) and N-tert-butoxycarbonylalanine (1020 mg, 5.4 mM) in dichloromethane (50 ml) were added benzotriazol-1-yloxytripyrrolidinophosphonium hexafluorophosphate (2800 mg, 5.6 mM) and N-methylmorpholine (1.2 ml, 11 mM). The mixture was stirred for 15 h at room temperature. Then the solvent was evaporated under vacuum, the residue suspended in water and extracted 3 times with ethyl acetate. The collected extracts were evaporated and then purified by flash chromatography on silica gel using as eluant cyclohexane/ethylacetate 1:9. Thus pure 5-(N-tert-butoxycarbonylalanylamino)-2-oxindole was obtained (600 mg). A solution of the above compound (250 mg, 0.97 mM) in trifluoroacetic acid (15 ml) was maintained for 1 h at room temperature. Then the solution was concentrated under vacuum and ether added to precipitate 5-(alanylamino)-2-oxindole.

The precipitate (200 mg, 0.97 mM) was suspended with N-tert-butoxycarbonylalanine (190 mg, 1 mM) in dichloromethane (10 ml) to which benzotriazol-1-yloxy-tripyrrolidinophosphonium hexafluorophosphate (520 mg, 1 mM) and N-methylmorpholine (0.35 ml, 3 mM) was added. After 36 h stirring at room temperature the raw product was extracted with ethylacetate and then purified by flash chromatography using ethylacetate as eluant. Thus 230 mg of N-tert-butoxycarbonylalanylalanylamino-2-oxindole were obtained.

To a solution of the above compound (230 mg, 0.59 mM) in absolute ethanol (10 ml) 1,4-dihydroxytetralin-2-aldehyde (113.5 mg, 0.59 mM) and piperidine (0.059 ml, 0.59 mM) was added and the resulting solution was refluxed for 2 h. Then the ethanol was evaporated and the residue was purified by flash chromatography using cyclohexane/ethylacetate 9:1 as eluant thus giving 90 mg of 5-(N-tert-butoxycarbonylalanylalanylamino)-3-(1,4-dihydroxy-2-tetralylmethylen)-2-oxindole.

The above compound was deblocked with trifluoroacetic acid as described above. The raw product was purified by reverse phase chromatography using as eluant ammoniumacetate 0.1 M/methanol 6:4. Thus pure title compound was obtained in 90% yield.

FD-MS: 464 (100, [M]+), 394 (45, M-COCH(CH3)NH2+2H]+)

NMR δ ppm (400 MHz, DMSO): 1.11 (d, J=7.0 Hz, 3H), 1.24 (d, J=7.0 Hz, 3H), 1.67 (m, 4H), 1.86 (s, 3H), 2.56 (m, 4H), 3.27 (m, 1H), 4.38 (m, 1H), 6.77 (d, J=8.5 Hz, 1H), 6.94 (s, 1H), 7.64 (dd, J=2.1/8.5 Hz, 1H), 7.66 (s, 1H), 7.72 (d, J=2.1 Hz, 1H), 8.1 (bs, 1H), 9.86 (s, 1H), 10.4 (bs, 1H).

By proceeding analogously the following compound can be prepared:

5-(glycylglycylamino)-3-(1,4-dihydroxy-2-tetralylmethylen)-2-oxindole.

EXAMPLE 8

1,4-dihydroxytetralin-2-aldehyde

To a solution of 1,4-naphthoquinone (10 g, 63.3 mM) in glacial acetic acid were added platinum oxide (0.75 g, 3.3 mM) and the mixture was hydrogenated in a Parr apparatus under a pressure of 30–40 psi for about 24 h at room temperature. The catalyst was filtered off, the acetic acid was evaporated under vacuum, the residue was dissolved in hot water (200 ml) and the solution cooled to give crystalline 1,4-dihydroxytetralin in 58.3% yield (4.0 g).

To a solution of 1,4-dihydroxytetralin (1.640 g, 10 mM), in dichloromethane (50 ml) was added titanium tetrachloride (5.69 g, 30 mM). Then 1,1-dichlorodimethyl ether (1.73 g, 15 mM) was added dropwise under vigorous stirring and the reaction mixture stirred for another 3 h at room temperature. Finally 5% hydrochloric acid (10 ml) was added under ice-cooling. The organic phase was separated and the residual aqueous phase repeatedly extracted with ether. The combined organic phases are washed with saturated saline solution, dried over sodium sulfate and evaporated under vacuum. The residue was crystallized from benzene or alternatively submitted to flash chromatography on silica gel with benzene ethylacetate 85:15, to afford pure title compound in about 60% yield (1.080 g), m.p. 145° C.

MS m/z 192

NMR δ ppm: 10.4 (bs, OH), 9.7 (s, —CHO), 9.1 (bs, OH), 6.9 (s, H arom), 2.8 (m, 5-$CH_2$, 8-$CH_2$), 1.9(m, 6-$CH_2$, 7-$CH_2$).

EXAMPLE 9

5-tert-butoxycarbonylamino-2-oxindole

To a stirred solution of 5-nitro-2-oxindole (2.27 g, 14 mM) in tert-butanol (120 ml) was added portionwise pyridinium bromide perbromide (16.2 g, 50 mM) over a period of 0.5 h. The reaction mixture was stirred for 4 h at room temperature with occasional warming to prevent tert-butanol from freezing. Tertbutanol was removed in vacuum and the resulting residue dissolved in ethylacetate/water. The organic phase was separated and the aqueous layer extracted once more with ethylacetate. The combined organic extracts were washed with water 2 times, dried over sodium sulfate and concentrated in vacuum. Trituration of the crude product with dichloromethane gave almost pure 3.3-dibromo-5-nitro-2-oxindole in 88% yield (4.139 g), m.p. 205° C.

To the above compound (4.139 g, 12.3 mM) dissolved in acetic acid (70 ml) was added portionwise under stirring zinc dust (5.884 g, 90 mM) at 0–5° C. and the mixture was stirred for another 1 h. The mixture was filtered on a pad of celite, the pad washed with ethylacetate, the separated organic layer washed with 5% sodium bicarbonate solution and brine, dried and evaporated to dryness to give raw 5-amino-2-oxindole in about 75% yield (1.368 g). To the above compound (1.368 g, 9.23 mM) dissolved in dioxane (40 ml) was added triethylamine (1.923 g, 19 mM) and di-tertbutyl-dicarbonate (2.073 g, 9.5 mM) and the solution was stirred for 4 h at room temperature. Then the solution was concentrated under reduced pressure, the residue taken up in dichloromethane, the organic phase washed with water, dried and evaporated under vacuum. The residue was chromatographed on silica gel using cyclohexane/ethylacetate 7:3 as eluant to give pure title compound in about 80% yield (1.833 g).

$C_{13}H_{16}N_2O_3$ calcd: C62.89 H6.50 N11.28 found: C62.85 H6.45 N11.15

FD-MS (m/z): 248 (100, [M]+)

EXAMPLE 10

Tablets each weighing 0.150 g and containing 25 mg of the active substance, can be manufactured as follows:
Composition (for 10,000 tablets):

| | |
|---|---|
| 5-(alanylamino)-3-(1,4-dihydroxy-2-tetralylmethylen)-2-oxindole | 250 g |
| Lactose | 800 g |
| Corn starch | 415 g |
| Talc powder | 30 g |
| Magnesium stearate | 5 g |

The 5-(alanylamino)-3-(1,4-dihydroxy-2-tetralylmethylen)-2-oxindole, the lactose and half of the corn starch are mixed; the mixture is then forced through a sieve of 0.5 mm mesh size. Corn starch (10 g) is suspended in warm water (90 ml) and the-resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 11

Capsules, each dosed at 0.200 g and containing 20 mg of the active substance can be prepared.
Composition for 500 capsules:

| | |
|---|---|
| 5-(glutamylamino)-3-(1,4-dihydroxy-2-tetralylmethylen)-2-oxindole | 1.0 g |
| Lactose | 80 g |
| Corn starch | 5 g |
| Magnesium stearate | 5 g |

This formulation is encapsuled in two-piece hard gelatin capsules and dosed at 0.200 g for each capsule.

What is claimed is:

1. A tetralylmethylene-2-oxindole derivative having the following formula (I)

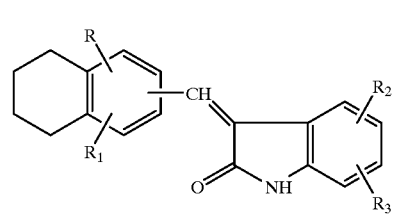

(I)

wherein
one or two of R, $R_1$, $R_2$ and $R_3$, the said two being the same or different, are selected from:
a) —X—$(CH_2)_m$—$NH_2$, —X—$(CH_2)_m$$NR_4R_5$ or —X—$(CH_2)_m$—$NHR_6$, in which X is —O—, —S— or —NH—, m is an integer of 2 to 4, one of $R_4$ and $R_5$ is hydrogen or $C_1$–$C_6$ alkyl and the other is $C_1$–$C_6$ alkyl or $R_4$ and $R_5$ taken together with the N atom to which they are linked form a 5 to 7 membered saturated heteromonocycle, and $R_6$ is $C_2$–$C_6$ alkanoyl or a C-terminally linked peptidyl group consisting of 1 to 3 aminoacids wherein the terminal amino group is either free or protected or in an alkylated form to provide a —$NR_4R_5$ group in which $R_4$ and $R_5$ are as defined above;

b) —NH—C(=NH)—NR$_4$R$_5$, —NH—C(=NH)—NHR$_6$, —N=CH—NH$_2$, —N=CH—NR$_4$R$_5$ or —N=CH—NHR$_6$ in which R$_4$, R$_5$ and R$_6$ are as defined above;

c) —X—(CH$_2$)$_n$—COR$_7$ wherein X is as defined above, n is an integer of 1 to 4, R$_7$ is hydroxy, amino, C$_1$–C$_6$ alkoxy or —NR$_4$R$_5$ in which R$_4$ and R$_5$ are as defined above or R$_7$ is a N-terminally linked peptidyl group consisting of from 1 to 3 aminoacids;

d) —COR$_a$ or —COR$_8$ in which R$_a$ is a N-terminally linked peptidyl group consisting of from 1 to 3 aminoacids and R$_8$ is —(CH$_2$)$_p$—NH$_2$, —(CH$_2$)$_p$—NR$_4$R$_5$ or —(CH$_2$)$_p$—NHR$_6$ in which p is 1 or 2 and R$_4$, R$_5$ and R$_6$ are as defined above;

e) —Y—CO—Y'—R$_9$ wherein each of Y and Y' which may be same or different is —NH— or —O— and R$_9$ is phenyl or C$_1$–C$_6$ alkyl unsubstituted or substituted by phenyl; and f) —NHR$_6$ or —NHR$_{10}$ in which R$_6$ is as defined above and R$_{10}$ is an amino protecting group; and the remainder of R, R$_1$, R$_2$ and R$_3$, which are the same or different, are selected from hydrogen, halogen, amino, hydroxy, C$_1$–C$_6$ alkyl, C$_1$–C$_6$ alkoxy, carboxy, C$_1$–C$_6$ alkoxycarbonyl, C$_2$–C$_6$ alkanoyloxy, cyano and —NR$_4$R$_5$ in which R$_4$ and R$_5$ are as defined above, or a pharmaceutically acceptable salt of a salt forming derivative of formula (I) as defined above.

2. A compound according to claim 1, wherein one of R, R$_1$, R$_2$ and R$_3$ is selected from:

a') —X—(CH$_2$)$_m$—NH$_2$, —X—(CH$_2$)$_m$—NR$_4$R$_5$ or —X—(CH$_2$)$_m$—NHR$_6$ in which X is oxygen or —NH—, m is 2, one of R$_4$ and R$_5$ is C$_1$–C$_4$ alkyl and the other is hydrogen or C$_1$–C$_4$ alkyl or R$_4$ and R$_5$ taken together with the nitrogen atom to which they are linked form a piperidine or morpholine ring, and R$_6$ is a C-terminally linked peptidyl group consisting of 1 or 2 aminoacids;

b') —NH—C(=NH)—NR$_4$R$_5$, —N=CH—NR$_4$R$_5$ in which one of R$_4$ and R$_5$ is C$_1$–C$_4$ alkyl and the other is hydrogen or C$_1$–C$_4$ alkyl;

c') —X—(CH$_2$)$_n$—COR$_7$ in which X is —O— or —NH—, n is 1 or 2, R$_7$ is amino or a N-terminally linked peptidyl group consisting of 1 or 2 aminoacids;

d') —COR$_a$ or —COR$_8$ in which R$_a$ is as defined above and R$_8$ is —(CH$_2$)$_p$—NH$_2$ or —(CH$_2$)$_p$—NR$_4$R$_5$ in which p is 1 or 2 and one of R$_4$ and R$_5$ is C$_1$–C$_4$ alkyl and the other is hydrogen or C$_1$–C$_4$ alkyl or R$_4$ and R$_5$ taken together with the nitrogen atom to which they are linked form a piperidine or morpholine ring; and e') —NHR$_6$ or —NHR$_{10}$ in which R$_6$ is C$_2$–C$_4$ alkanoyl or a C-terminally linked peptidyl group consisting of 1 or 2 aminoacids and R$_{10}$ is an amino protecting group; and the remainder of R, R$_1$, R$_2$ and R$_3$, which are the same or different, are selected from hydrogen, halogen, amino, hydroxy, C$_1$–C$_4$ alkyl, C$_1$–C$_4$ alkoxy, C$_1$–C$_4$ alkoxy-carbonyl, C$_2$–C$_4$ alkanoyloxy, cyano C$_1$–C$_4$ alkylamino and di-C$_1$–C$_4$ alkylamino.

3. A compound selected from:

5-(tert-butoxycarbonylamino)-3-(1,4-dihydroxy-2-tetralylmethylen)-2-oxindole;

5-glycylamino-3-(1,4-dihydroxy-2-tetralylmethylen)-2-oxindole;

5-(glycylglycylamino)-3-(1,4-dihydroxy-2-tetralylmethylen)-2-oxindole;

5-(alanylamino)-3-(1,4-dihydroxy-2-tetralylmethylen)-2-oxindole;

5-(alanylalanylamino)-3-(1,4-dihydroxy-2-tetralylmethylen)-2-oxindole;

5-(N-tert-butoxycarbonylalanylamino)-3-(1,4-dihydroxy-2-tetralylmethylen)-2-oxindole;

5-(threonylamino)-3-(1,4-dihydroxy-2-tetralylmethylen)-2-oxindole;

5-(glutamylamino)-3-(1,4-dihydroxy-2-tetralylmethylen)-2-oxindole;

5-(2-dimethylaminoethylamino)-3-(1,4-dihydroxy-2-tetralylmethylen)-2-oxindole;

5-(2-morpholinoethylamino)-3-(1,4-dihydroxy-2-tetralylmethylen)-2-oxindole;

5-(2-glycylaminoethylamino)-3-(1,4-dihydroxy-2-tetralylmethylen)-2-oxindole;

5-(2-alanylamino-ethylamino)-3-(1,4-dihydroxy-2-tetralylmethylen)-2-oxindole;

5-(3,3-dimethylguanidino)-3-(1,4-dihydroxy-2-tetralylmethylen)-2-oxindole;

5-(dimethylaminomethylenamino)-3-(1,4-dihydroxy-2-tetralylmethylen)-2-oxindole;

N-[3-(1,4-dihydroxy-2-tetralylmethylen)-2-oxindol-5-yl] glycyl-alanine;

N-[3-(1,4-dihydroxy-2-tetralylmethylen)-2-oxindol-5-yl] glycyl-glycine;

N-[3-(1,4-dihydroxy-2-tetralylmethylen)-2-oxindol-5-ylcarbonyl]glycine;

N-[3-(1,4-dihydroxy-2-tetralylmethylen)-2-oxindol-5-ylcarbonyl]alanine;

5-(2-aminoacetyl)-3-(1,4-dihydroxy-2-tetralylmethylen)-2-oxindole;

5-(2-morpholinoacetyl)-3-(1,4-dihydroxy-2-tetralylmethylen)-2-oxindole;

3-[4-(2-glycylaminoethoxy)-1-tetralylmethylen])-2-oxindole;

3-[4-(2-alanylaminoethoxy)-1-tetralylmethylen]-2-oxindole;

3-[4-(2-morpholinoethoxy)-1-tetralylmethylen]-2-oxindole;

N-[1-(2-oxindol-3-ylmethylen)-4-tetralyloxyacetyl]glycine;

3-(4-glycylamino-1-tetralylmethylen)-2-oxindole; and 3-(4-alanylamino-1-tetralylmethylen)-2-oxindole; and the pharmaceutically acceptable salts of salt-forming members thereof; and wherein the compounds may, when appropriate, exist either as a Z- or E-diastereoisomer or as a Z,E- mixture thereof.

4. A process for producing a compound as defined in claim 1, which process comprises:

a) reacting an aldehyde of formula (II)

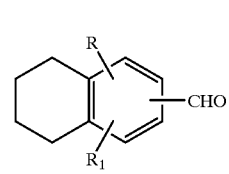

(II)

wherein R and R$_1$ are as defined in claim 1, with a compound of formula (III)

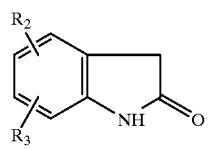

wherein $R_2$ and $R_3$ are as defined in claim 1; or b) reacting a compound of formula (IV)

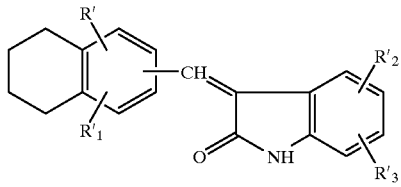

wherein one or two of R', $R'_1$, $R'_2$ and $R'_3$ are OH, —$NH_2$ or —SH and the remainder are as R, $R_1$, $R_2$ and $R_3$ as defined in claim 1, with an alkylating agent of formula (V) selected from Z—$(CH_2)_m$—$NH_2$;

Z—$(CH_2)_m$—$NR_4R_5$;

Z—$(CH_2)_m$—$NHR_6$; and

Z—$(CH_2)_n$—$COR_7$;

in which Z is a halogen atom and m, n, $R_4$, $R_5$, $R_6$ and $R_7$ are as defined in claim 1, thus obtaining a compound of formula (I) wherein one or two of R, $R_1$, $R_2$ and $R_3$ are as defined in claim 1 under a) or c); or c) reacting a compound of formula (VI)

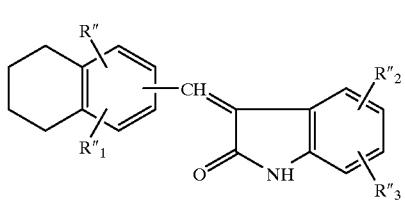

wherein one or two of R", $R''_1$, $R''_2$ and $R''_3$ are —OH or —$NH_2$ and the others are as R, $R_1$, $R_2$ and $R_3$ as defined in claim 1, with an acylating agent of formula (VII) selected from

HOOC—Y'—$R_9$

HOOC—$R_a$;

HOOC—$R_8$;

or a reactive carbonyl group thereof, wherein $R_a$, $R_8$, Y' and $R_9$ are as defined in claim 1, thus obtaining a compound of formula (I) wherein one or two of R, $R_1$, $R_2$ and $R_3$ are as defined in claim 1 under d) or e); and, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound of formula (I), and/or, if desired, separating a mixture of isomers of a compound of formula (I) into the single isomers.

5. A pharmaceutical composition comprising a suitable carrier and/or diluent, and, as an active principle, a compound as defined in claim 1.

6. A pharmaceutical composition comprising a compound of formula (I) as defined in claim 1, an additional antitumour agent and a pharmaceutically accepted carrier.

7. A method of treating a patient in need of a tyrosine kinase inhibitor, comprising administering to said patient a therapeutically effective amount of a compound of formula (I), as defined in claim 1 or a pharmaceutically acceptable salt thereof.

8. A method of inhibiting a tyrosine kinase comprising administering an amount of the compound of claim 1 effective to inhibit the tyrosine kinase.

9. A method of inhibiting metastasis comprising administering an amount of the compound of claim 1 effective for inhibition.

10. A method of inhibiting atheromatous plaque formation comprising administering an amount of the compound of claim 1 effective for inhibition.

11. A method of controlling angiogenesis comprising administering an amount of the compound of claim 1 effective for controlling angiogenesis.

12. A method of inhibiting pathological proliferative disorders comprising administering an amount of the compound of claim 1 effective for inhibition.

13. A method of inhibiting cancer comprising administering an amount of the compound of claim 1 effective for inhibition.

14. A method of inhibiting Alzheimer's disease comprising administering an amount of the compound of claim 1 effective for inhibition.

15. A method of inhibiting cancer comprising administering an amount of the compound of claim 6 effective for inhibition.

16. The composition of claim 6, wherein the additional antitumour agent is selected from the group consisting of: doxorubin, daunomycin, epirubicin, idarubicin, etoposide, fluorouracil, melphaln, cyclophosphamide, bleomycin, vinblastin, mitomycin and a mixture of two or more thereof.

* * * * *

UNITED STATES PATENT AND TRADEMARK OFFICE
CERTIFICATE OF CORRECTION

PATENT NO. : 6,147,073

DATED : November 14, 2000

INVENTOR(S): Carlo BATTISTINI, et al.

It is certified that an error appears in the above-identified patent and that said Letters Patent is hereby corrected as shown below:

On the title page, item [54], and Column 1, the title is listed incorrectly. Item [54] and column 1 should read as follows:

--[53] SUBSTITUTED TETRALYLMETHYLEN-OXINDOLE ANALOGUES AS TYROSINE KINASE INHIBITORS--

Signed and Sealed this

First Day of May, 2001

Attest:

NICHOLAS P. GODICI

*Attesting Officer*  *Acting Director of the United States Patent and Trademark Office*